US00PP22795P2

(12) United States Plant Patent
Harris et al.

(10) Patent No.: US PP22,795 P2
(45) Date of Patent: Jun. 19, 2012

(54) AZALEA PLANT NAMED 'MNIHAR019'

(50) Latin Name: ***Rhododendron* sp.**
Varietal Denomination: MNIHAR019

(76) Inventors: James O. Harris, Lawrenceville, GA (US); Ella Ruth Harris, Lawrenceville, GA (US)

( * ) Notice: Subject to any disclaimer, the term of this patent is extended or adjusted under 35 U.S.C. 154(b) by 0 days.

(21) Appl. No.: 12/932,431

(22) Filed: Feb. 25, 2011

(51) Int. Cl.
*A01H 5/00* (2006.01)

(52) U.S. Cl. ..... Plt./238

(58) Field of Classification Search ..... Plt./238
See application file for complete search history.

*Primary Examiner* — Annette Para
(74) *Attorney, Agent, or Firm* — Jondle & Associates, P.C.

(57) ABSTRACT

A new and distinct variety of Azalea plant with spring and fall blooming; attractive, showy, single red-orange flowers; easily propagated by semi-hardwood cuttings in late spring through summer; moderate growth rate under normal fertilization and moisture conditions; broadly-rounded and freely-branching in habit; grows well in containers; thrives in shade or sun; and is hardy in Zone 6, is disclosed.

2 Drawing Sheets

Genus and species: *Rhododendron* sp.
Variety denomination: 'MNIHAR019'.

BACKGROUND OF THE NEW PLANT

The present invention is a new and distinct variety of evergreen Azalea of the genus *Rhododendron*. This new Azalea, hereinafter referred to as 'MNIHAR019', was discovered in 2003 in Lawrenceville, Ga. 'MNIHAR019' originated from a planned cross hybridization in 2000 between the female azalea plant 'MNIKRI' U.S. Plant Pat. No. 17,229 (patented) and the male azalea plant 'Conleb' U.S. Plant Pat. No. 10,581 (patented) in a controlled environment in Lawrenceville, Ga. The present invention has a blooming period in early April and mid August until frost, an open, broadly globose growth habit, and cold hardiness.

The new plant was first propagated via semi-hardwood cuttings in 2004 in Dearing, Ga. and has been asexually reproduced repeatedly by semi-hardwood cuttings in Dearing, Ga. for over 6 years. 'MNIHAR019' has been found to retain its distinctive characteristics through successive asexual propagations via semi-hardwood cuttings.

'MNIHAR019' has not been made publicly available or sold more than one year prior to the filing date of this application.

SUMMARY OF THE INVENTION

The following are the most outstanding and distinguishing characteristics of this new cultivar when grown under normal horticultural practices in Dearing, Ga.

1. Spring and fall blooming;
2. Attractive, showy, red-orange colored flowers;
3. Numerous single flowers;
4. Easily propagated by semi-hardwood cuttings in late spring through summer;
5. Moderate growth rate under normal fertilization and moisture conditions;
6. Open, broadly globose growth habit;
7. Grows well in containers;

8. Thrives in shade or sun; and
9. Hardy in Zone 6.

DESCRIPTION OF THE PHOTOGRAPHS

This new Azalea hybrid variety is illustrated by the accompanying photographs which show buds, flowers, immature foliage and mature foliage. The colors shown are as true as can be reasonably obtained by conventional photographic means. The photographs are of five-year-old plants grown in filtered shade and full sun in 2008 and 2009 in Dearing, Ga.

DETAILED BOTANICAL DESCRIPTION OF THE NEW PLANT

Figure 1:
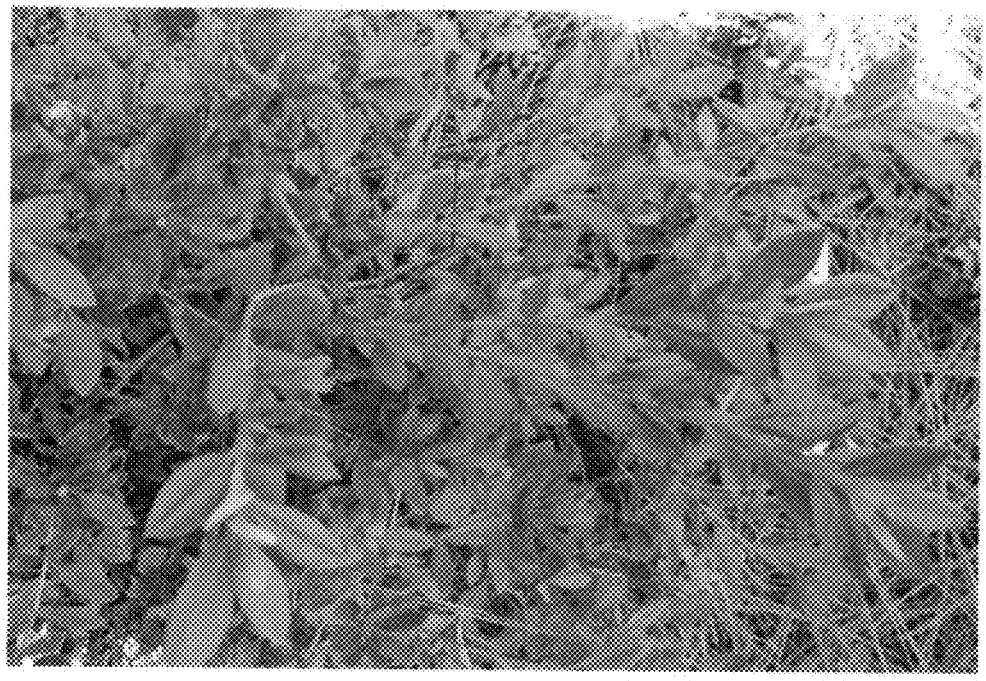
FIG. 1 is a close-up showing mature and immature foliage.
Figure 2:
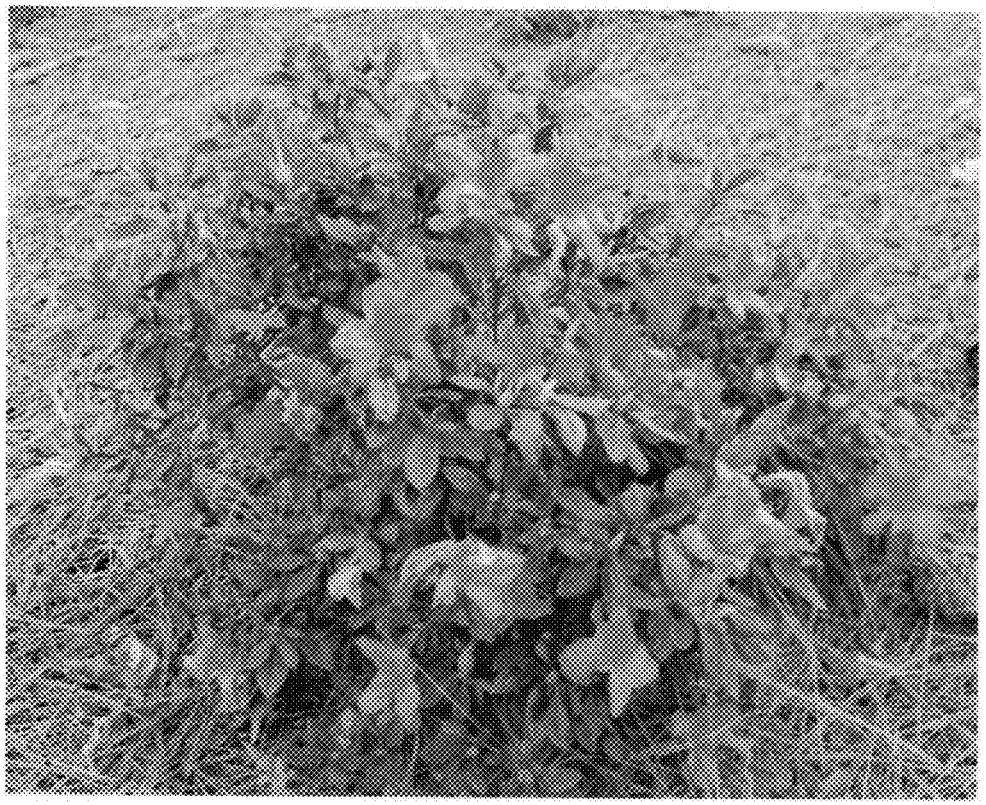
FIG. 2 shows mature foliage and growth habit and fall flowering of a four year old plant.
Figure 3:
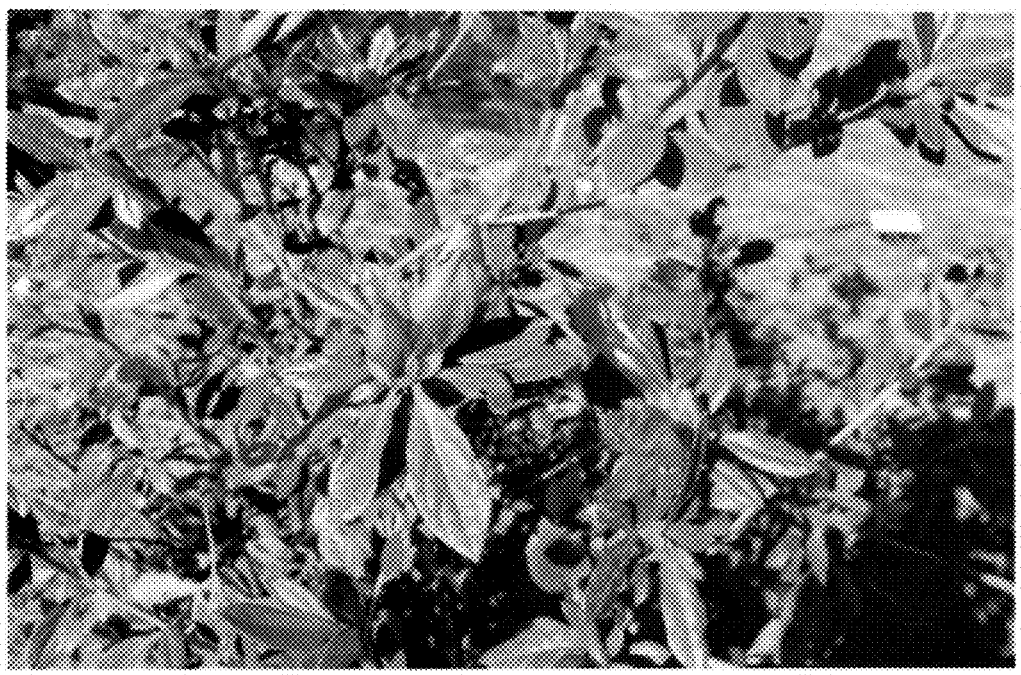
FIG. 3 is a close-up showing flower buds.
Figure 4:
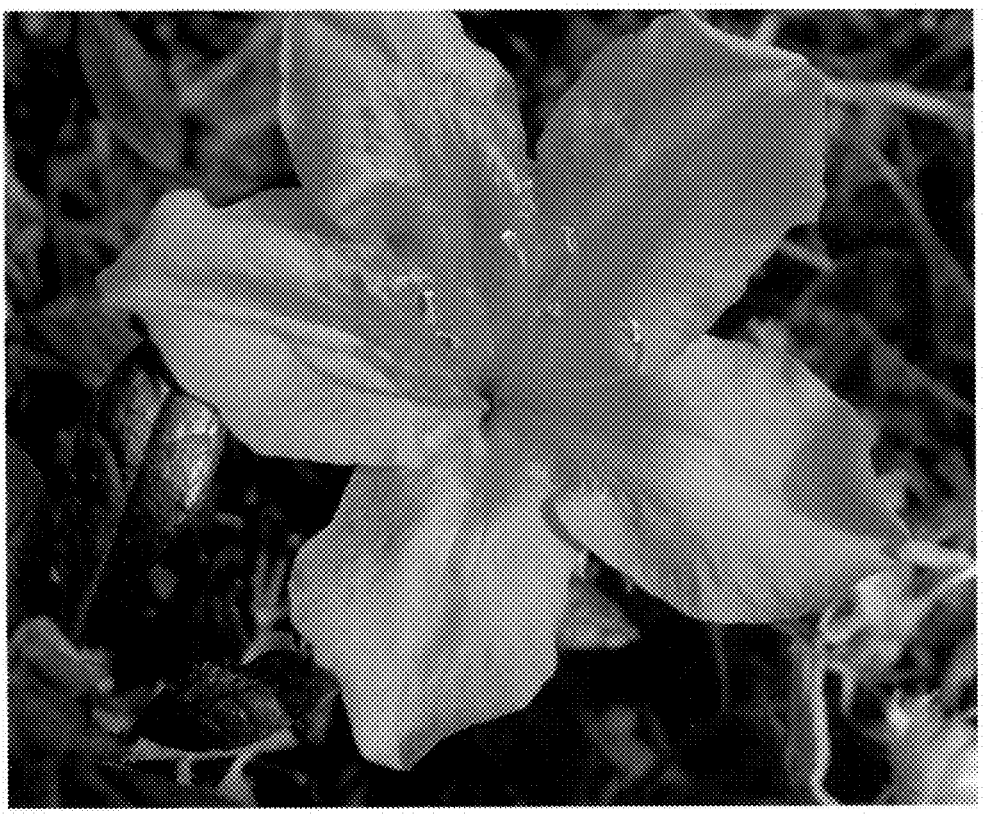
FIG. 4 is a close-up showing flower size, form, and color.

The following is a detailed description of the new variety of Azalea based on observations made of three-year-old plants grown in trade and three-gallon containers according to wholesale commercial production conditions, under full-sun and in an evaluation bed under semi-shade conditions in Dearing, Ga. in the spring, summer, and fall seasons of 2008, 2009, and 2010. The colors of the various plant parts are detailed with reference to The Royal Horticultural Society Colour Chart (2001).

Classification:
- *Family*.—Ericaceae.
- *Species*.—*Rhododendron* sp.
- *Common name*.—Azalea.
- *Commercial name*.—'MNIHAR019'.

Parentage:
- *Female parent*.—The azalea plant 'MNIKRI' U.S. Plant Pat. No. 17,229 (patented).
- *Male parent*.—The azalea plant 'Conleb' U.S. Plant Pat. No. 10,581 (patented).

Growth:
- *Form*.—Open, broadly globose.
- *Texture*.—Medium.

*Height*.—106.68 cm to 137.16 cm.

*Width*.—152.4 cm to 182.88 cm.

*Growth habit*.—Freely-branching; open and airy in nature.

*Growth rate*.—Moderate growth rate under normal fertilization and moisture conditions. In a period of 5 years from a rooted cutting the plant reaches a height of 71 cm and a spread of 91.44 cm. The growth rate is normally averages about 14.6 cm per year; the plant reaches a height of 106.68 cm to 137.16 cm at maturity while maintaining an open airy habit due to the abundant macrocladous branch development.

*Spring growth*.—The date of initial spring growth is March 26, followed by continuous growth through fall.

*Life cycle*.—Perennial and evergreen.

Leaves:

*Arrangement*.—Alternate, simple, pubescent, and evergreen.

*Shape*.—Oblanceolate to elliptic.

*Apex*.—Mucronate.

*Base*.—Attenuate.

*Margin*.—Entire.

*Length*.—4 cm.

*Width*.—1.8 cm.

*Venation pattern*.—Pinnate; the mid-veins and laterals are impressed on the upper surface and the prominent on the lower surface.

*Immature leaf*.—Upper surface: Color: Matte to Semi-glossy, RHS 144A (yellow-green). Pubescence: Scabrous with some strigose concentrated along the mid-vein. Pubescence color: RHS 155C (white). Lower surface: Color: Matte to Semi-glossy, RHS 144B (yellow-green). Pubescence: Scabrous with strigose concentrated along the veins. Pubescence color: RHS 155C (white).

*Mature leaf*.—Upper surface: Color: Semi-glossy to Matte, RHS 139A (green). Pubescence: Moderate amount of scabrous with some strigose along veins and margin. Pubescence color: RHS 166A (greyed-orange). Lower surface: Color: Matte, RHS 146B (yellow-green). Pubescence: Strigose with some scabrous. Pubescence color: RHS 166C (greyed-orange).

*Petiole*.—Length: 0.5 cm. Diameter: 0.15 cm. Pubescence: Strigose. Length: 0.1 cm. Color: Immature: RHS 155C (white) to RHS 164A (greyed-orange). Mature: RHS 166B (greyed-orange). Color: Immature: RHS 145A (yellow-green). Mature: RHS 144B (yellow-green).

Stems:

*Form*.—Branched at terminal buds with some from auxiliary buds at leaf nodes.

*Young stems* (*1-year-old and younger*).—Color: RHS 145C (yellow-green) to RHS 145B (yellow-green). Pubescence: Strigose. Pubescence color: Begins RHS 157C (green-white) maturing to RHS 165B (greyed-orange).

*Second-year stems*.—Color: RHS N199C (grey-brown) with areas of RHS 197A (greyed-green). Pubescence: Strigose to tomentose, the quantity decreases with age of the stem. Pubescence color: RHS 165A (greyed-orange) in color. Length: 12 cm on average. Diameter: 0.3 cm. Pith: Solid and uniform. Internode length: 0.6 cm to 1.2 cm.

Flower buds:

*Arrangement and form*.—At terminal; borne in groups of two or three, sheathed by one to three modified leaf bracts. Length: Average 1.8 cm. Width: 0.7 cm. Color: RHS N144D (yellow-green) with areas of RHS 139A (green) and RHS 145C (yellow-green). Shape: Ovate.

*Apex*.—Acute.

*Base*.—Rounded.

*Length* (*at tight bud*).—1.3 cm.

*Diameter* (*at tight bud*).—0.5 cm.

*Color* (*of scales*).—Immature: RHS 149D (yellow-green). Mature: RHS 149D (yellow-green) to RHS 144C (yellow-green).

*Texture*.—Matte; strigose pubescence. Pubescence color: RHS N167A (greyed-orange).

*Pedicel*.—Length: 0.6 cm at point bud begins to open. Diameter: 0.2 cm. Texture: Pubescent, Pilose pubescence. Pubescence color: RHS N155D (white) to RHS 165C (greyed-orange). Color: RHS 145A (yellow-green) with slight RHS 46A (red) areas near the base of Calyx.

*Calyx*.—Length: 0.8 cm. Diameter: 0.3 cm. Texture: Pubescent, Sericeous pubescence. Pubescence color: RHS 155D (white). Color: RHS 144B (yellow-green).

Flowers:

*Type*.—Perfect, Single flowers.

*Shape*.—Open funnel-shaped.

*Flowering habit and period*.—Borne on the current season's growth; Two weeks beginning in early April in Dearing, Ga.; flowering resumes mid August and continues until frost which can be as late as November or December.

*Lastingness of flowers on the plant*.—4 to 6 days in the sun; 4 to 7 days in the shade.

*Fragrance*.—Absent.

*Diameter*.—8 cm.

*Depth*.—4.2 cm.

*Petals*.—Quantity per flower and arrangement: Five imbricate petals that are fused at the base and remain fused up to 3 cm from the base. Shape: Obovate. Apex: Rounded with some retuse. Base: Fused. Margin: Entire, undulate. Texture (both upper and lower surfaces): Glabrous. Length (of petals without spots): 5.5 cm. Width (of petals without spots): 2.8 cm. Color: Upper surfaces: RHS 39A (red) the upper surface of the spots are RHS 46A (red). Lower surfaces: RHS N34C (orange-red), lower surface of spots are RHS 46D (red).

Reproductive parts:

*Pistil*.—Quantity and form: Single, Non-petaloid. Length: 4.8 cm. Diameter: 0.075 cm. Stigma: Color: RHS 53A (red). Diameter: 0.15 cm. Style color: RHS 47B (red). Ovary: Pubescent, pilose with 5 locules. Color: RHS N155D (white).

*Stamens*.—Number: 6 per flower; non-petaloid. Length: 4.1 cm. Color: RHS 47C (red) to RHS 47D (red). Anther: Length: 0.2 cm. Width: 0.1 cm. Color: RHS 166A (greyed-orange) with areas of RHS 178A (greyed-red). Pollen: Moderate. Color: RHS 4D (yellow).

Fruit:

*Maturity*.—The capsule matures in about 6 months in Dearing, Ga. and the fruit set is moderate and contains about 100 to 150 non-winged seeds.

*Length.*—1.3 cm.
*Width.*—0.7 cm.
*Color.*—RHS 146B (yellow-green).

CULTURE

'MNIHAR019' grows well in a wide range of conditions and tolerates sun to shade. 'MNIHAR019' prefers moist, well-drained soil that is rich in organic matter and responds well to mulching and medium applications of fertilizer. 'MNIHAR019' does best in soil with a pH of 5.0 to 5.5 and is propagated with semi-hardwood cuttings in late spring through the summer. Azaleas root in five to six weeks with a high percentage of rooting (80% plus). Tissue culture is also an effective means of propagation for azaleas.

DISEASES AND INSECTS

Lace bugs, root weevils, and spider mites can be a problem. Fungal and bacterial pathogens have not been observed, but no resistance testing has been performed and no claim to abnormal resistance to pathogens can be made.

COMPARISON WITH PARENTAL AND COMMERCIAL VARIEITES

In Table 1, the 'MNIHAR019' is compared to parental varieties 'MNIKRI' U.S. Plant Pat. No. 17,229 (patented) and 'Conleb' U.S. Plant Pat. No. 10,581 (patented) and lists the differences between the varieties.

TABLE 1

| Characteristic | 'MNIHAR019' | 'MNIKRI' U.S. Plant Pat. No. 17,229 | 'Conleb' U.S. Plant Pat. No. 10,581 |
|---|---|---|---|
| Plant Height (Mature) | 106.68 cm to 137.16 cm | 76.2 cm to 91.44 cm | 121.92 cm to 152.4 cm |
| Flower Diameter | 8 cm | 7.62 inches | 6.5 cm |
| Flower Form | Single | Single/hose-in-hose/semi-double | Single to semi-double |
| Flower Color | Red-orange | Light Pink | Red |
| Bloom Period | Early April and mid August until frost | April and September until frost | April and late July until frost |
| Hardy Zone | 6 | 5 | 7 |
| Stamen Number | 6 | 5 | 0 to 9 |
| Stamen Type | Non-petaloid | Petaloid | Petaloid and Non-petaloid |

When 'MNIHAR019' is compared to the commercial variety 'Roblen' (U.S. Plant Pat. No. 16,248), 'MNIHAR019' has an open, broadly globose growth habit with a height of 71 cm and a spread of 91.44 cm in 5 years, while 'Roblen' (U.S. Plant Pat. No. 16,248) has a height of 91.44 cm and a spread of 60.96 cm in six years. Additionally, 'MNIHAR019' produces red-orange flowers, while 'Roblen' has bright red flowers.

I claim:

1. A new variety of Azalea plant named 'MNIHAR019' as herein shown and described.

* * * * *